United States Patent
Helmer et al.

(10) Patent No.: US 11,524,121 B2
(45) Date of Patent: Dec. 13, 2022

(54) MEDICAMENT DELIVERY DEVICE

(71) Applicant: SANOFI, Paris (FR)

(72) Inventors: Michael Helmer, Frankfurt am Main (DE); Christian Rehbein, Budenheim (DE)

(73) Assignee: Sanofi, Paris (FR)

(*) Notice: Subject to any disclaimer, the term of this patent is extended or adjusted under 35 U.S.C. 154(b) by 281 days.

(21) Appl. No.: 16/753,248

(22) PCT Filed: Oct. 19, 2018

(86) PCT No.: PCT/EP2018/078685
§ 371 (c)(1),
(2) Date: Apr. 2, 2020

(87) PCT Pub. No.: WO2019/077098
PCT Pub. Date: Apr. 25, 2019

(65) Prior Publication Data
US 2020/0297937 A1 Sep. 24, 2020

(30) Foreign Application Priority Data
Oct. 19, 2017 (EP) ..................... 17306416

(51) Int. Cl.
*A61M 5/315* (2006.01)
(52) U.S. Cl.
CPC . *A61M 5/31568* (2013.01); *A61M 2205/3306* (2013.01)
(58) Field of Classification Search
CPC .......... A61M 5/31568; A61M 5/31556; A61M 2205/3306
See application file for complete search history.

(56) References Cited

U.S. PATENT DOCUMENTS

| 4,498,843 A | 2/1985 | Schneider et al. |
| 5,376,785 A * | 12/1994 | Chin ........................ G01D 5/34 250/227.21 |

(Continued)

FOREIGN PATENT DOCUMENTS

| CN | 1671432 | 9/2005 |
| CN | 104203315 | 12/2014 |

(Continued)

OTHER PUBLICATIONS

International Preliminary Report on Patentability in Application No. PCT/EP2018/078685, dated Apr. 21, 2020, 9 pages.

(Continued)

*Primary Examiner* — Tasnim Mehjabin Ahmed
(74) *Attorney, Agent, or Firm* — Fish & Richardson P.C.

(57) ABSTRACT

A medicament delivery device includes a housing configured to receive a container of medicament and a piston rod moveable within the housing and configured to engage a container of medicament when received within the housing. The medicament delivery device further includes a position-sensing mechanism configured to detect the position of the piston rod within the housing. The position-sensing mechanism includes a first light source configured to emit light, a first sensor disposed proximate the first light source and configured to receive light emitted by the first light source, and a blocking member moveable between the first light source and the first sensor. The first sensor is configured to detect the light pattern received to determine the position of the piston rod within the housing.

25 Claims, 7 Drawing Sheets

(56) References Cited

U.S. PATENT DOCUMENTS

| | | | |
|---|---|---|---|
| 5,792,117 A | 8/1998 | Brown | |
| 10,366,788 B2* | 7/2019 | Azapagic | G16H 20/17 |
| 2002/0122666 A1 | 9/2002 | Miyazaki et al. | |
| 2005/0139060 A1 | 6/2005 | Muramatsu | |
| 2005/0197626 A1* | 9/2005 | Moberg | A61M 5/14566 604/131 |
| 2009/0100993 A1 | 4/2009 | Komatsu | |
| 2009/0299279 A1 | 12/2009 | Richter | |
| 2012/0268741 A1 | 10/2012 | Pommereau et al. | |
| 2014/0194826 A1 | 7/2014 | Nielsen et al. | |

FOREIGN PATENT DOCUMENTS

| | | | |
|---|---|---|---|
| CN | 104755118 | 7/2015 | |
| CN | 106102800 | 11/2016 | |
| EP | 3155378 | 4/2017 | |
| EP | 2852813 | 9/2020 | |
| JP | 3381301 | 2/2003 | |
| JP | 2009-098582 | 5/2009 | |
| JP | 2017-508596 | 3/2017 | |
| JP | 2017-518819 | 7/2017 | |
| TW | 536656 | 6/2003 | |
| TW | 200831149 | 8/2008 | |
| WO | WO 2013/120778 | 8/2013 | |
| WO | WO 2013/177135 | 11/2013 | |
| WO | WO 2014/067879 | 5/2014 | |
| WO | WO 2015/143058 | 9/2015 | |
| WO | WO-2015143058 A1 * | 9/2015 | A61M 5/31568 |
| WO | WO 2015/189173 | 12/2015 | |
| WO | WO 2017/009724 | 1/2017 | |
| WO | WO 2017/114911 | 7/2017 | |

OTHER PUBLICATIONS

International Search Report and Written Opinion in Application No. PCT/EP2018/078685, dated Dec. 5, 2018, 11 pages.

* cited by examiner

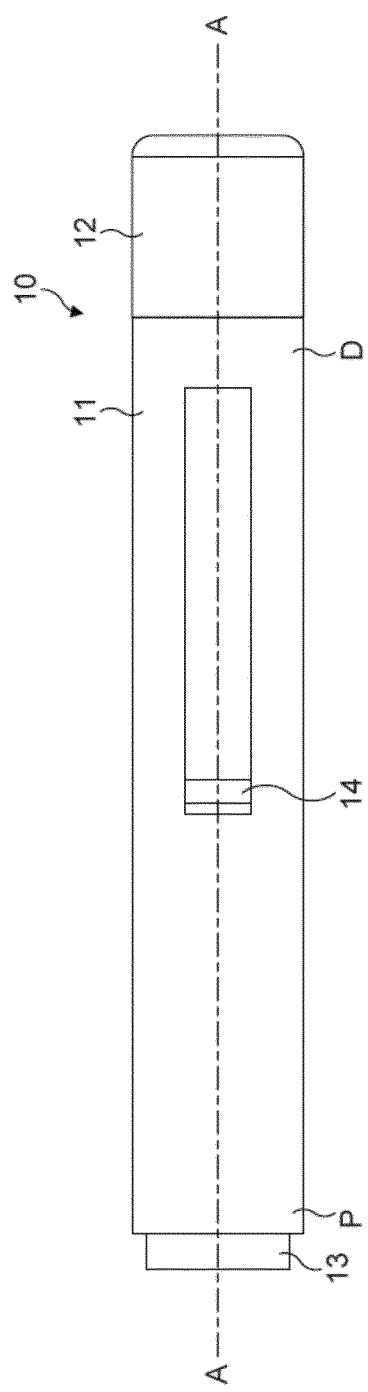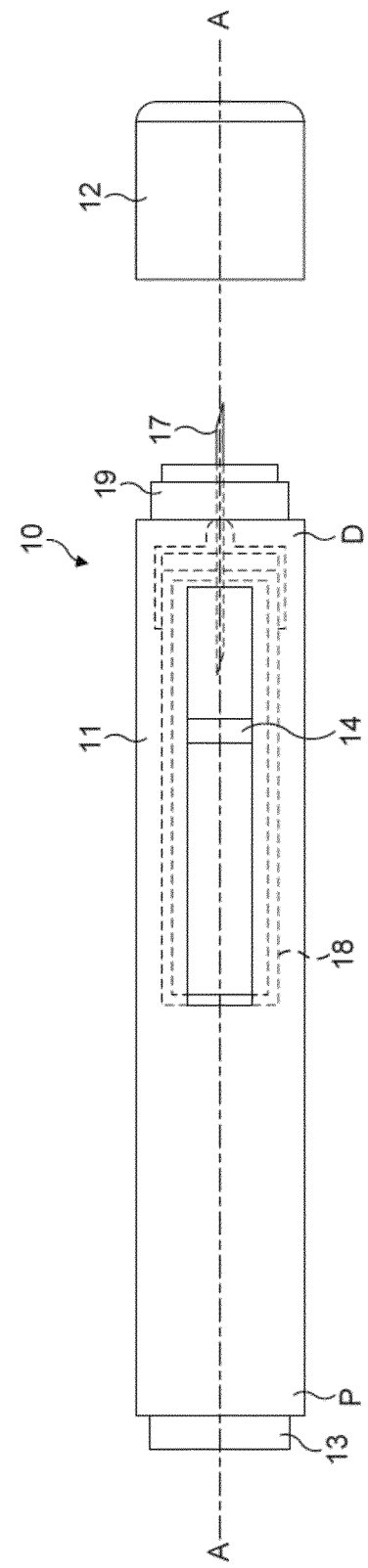

MEDICAMENT DELIVERY DEVICE

CROSS REFERENCE TO RELATED APPLICATIONS

The present application is the national stage entry of International Patent Application No. PCT/EP2018/078685, filed on Oct. 19, 2018, and claims priority to Application No. EP 17306416.3, filed on Oct. 19, 2017, the disclosures of which are incorporated herein by reference.

TECHNICAL FIELD

The present disclosure relates to a medicament delivery device.

BACKGROUND

Certain types of injection devices typically have a sealed container of medicament, a needle for injection of the medicament into a patient and a mechanism for dispensing the medicament from the container through the needle. Such dispensing mechanisms can include a plunger or piston which can be moved into the container to dispense the medicament.

SUMMARY

The present disclosure provides an improved medicament delivery device.

The present disclosure describes a medicament delivery device including a housing configured to receive a container of medicament, a piston rod moveable within the housing and configured to engage a container of medicament when received within the housing, and a position-sensing mechanism configured to detect the position of the piston rod within the housing, the position-sensing mechanism including a light source configured to emit light, and a sensor disposed proximate the light source and configured to receive light emitted by the light source, and a blocking member moveable between the light source and the sensor in dependence upon the movement of the piston rod, wherein the position-sensing mechanism is configured such that a varying light pattern reaches the sensor dependent on the position of the blocking member relative to the light source and the sensor, and wherein the sensor is configured to detect the light pattern received to determine the position of the piston rod within the housing.

The medicament delivery device may further include a projecting member extending from the piston rod. The projecting member may have a surface that is configured such that a distance from the surface to a longitudinal axis of the piston rod varies along the length of the piston rod.

The surface may be inclined relative to the axis of the direction of movement of the piston rod in the housing.

The projecting member may extend radially from the piston rod. The inclined surface may be at a radially outermost position of the projecting member. The light source and the sensor may be fixed relative to the housing.

The light source and the sensor may be arranged such that the light source is on a first side of the projecting member and the sensor is on the opposite side of the projecting member and the projecting member variably blocks light passing from the light source to the sensor.

The housing may include a piston rod guide having at least two projections between which the projecting member is located, and the projections may be configured to restrict rotational movement of the piston rod.

The piston rod may be engaged with a drive mechanism and may be configured to act upon a piston of a container of medicament when received within the medicament delivery device when the drive mechanism is activated.

The projecting member may be the blocking member and may be configured to be moveable between the light source and the sensor.

The blocking member may extend from a component on the opposite side of the drive mechanism to the piston rod, and the component may be engaged with the drive mechanism such that it is moveable within the housing when the drive mechanism is activated.

The position-sensing mechanism and the component maybe located in a separable portion of the housing and the drive mechanism may include a separable connection which is configured to separably connect a part of the drive mechanism which engages the piston rod in a first portion of the housing and a part of the drive mechanism that engages the component in a second portion of the housing.

The blocking member of the position-sensing mechanism may include a first blocking element that is moveable in a direction perpendicular to the direction in which the piston rod is moveable, and the first blocking element may be biased into contact with the surface of the projecting member, and the light source may include a first light source and the sensor may include a first sensor, and the first blocking element may include a first blocking portion configured such that the first blocking portion is moveable between the first light source and the first sensor. The first blocking portion may be configured such that a varying light pattern reaches the first sensor from the first light source dependent on the position of the first blocking element which is dependent on the position of the projecting member of the piston rod in the housing.

The position-sensing mechanism may further include a second blocking element located on the opposite side of the piston rod to the first blocking element and having a second blocking portion, the light source may include a second light source and the sensor may include a second sensor, the second blocking element may be moveable in a direction perpendicular to the direction in which the piston rod is moveable between a second light source and a second sensor, the second blocking element may be biased into contact with the body of the piston rod and configured such that a varying amount of light reaches the second sensor from the second light source dependent on the position of the second blocking portion which is dependent on the position of the piston rod in the housing.

The light source and the sensor may be arranged such that the light source is on a first side of the element and the sensor is on the opposite side of the element and the element is configured to block different amounts of light dependent on the position of the element in the direction of movement.

The first and/or second blocking element may include an aperture having a cross-sectional area that varies in the direction of movement of the first and/or second blocking element to block different amounts of light dependent on the position of the first and/or second blocking element in the direction of movement of the first and/or second blocking element.

The element may extend radially relative to the piston rod. The first and/or second light source may be a light-emitting diode. The first and/or second sensor may be a position sensitive detector or a charge-coupled device.

The medicament delivery device may further include a controller configured to receive a signal from the first and/or second sensor and determine the position of the piston rod in dependence on the received signal.

Optionally, the controller may be configured to output a position signal to a user interface representative of the determined piston rod position.

The medicament delivery device may be reusable. Alternatively, the medicament delivery device may be disposable. That is, the medicament delivery device may be configured to provide a predetermined number of doses before it is disposed of.

The medicament delivery device may further include a container of medicament.

These and other aspects will be apparent from and elucidated with reference to the embodiments described hereinafter.

BRIEF DESCRIPTION OF THE FIGURES

Embodiments of the disclosure will now be described, by way of example, with reference to the accompanying drawings.

FIG. 1A shows a schematic side view of a medicament delivery device, with a cap attached to a body of the device.

FIG. 1B shows a schematic side view of the device of FIG. 1A, with the cap removed from the body.

DETAILED DESCRIPTION

Figure 2:
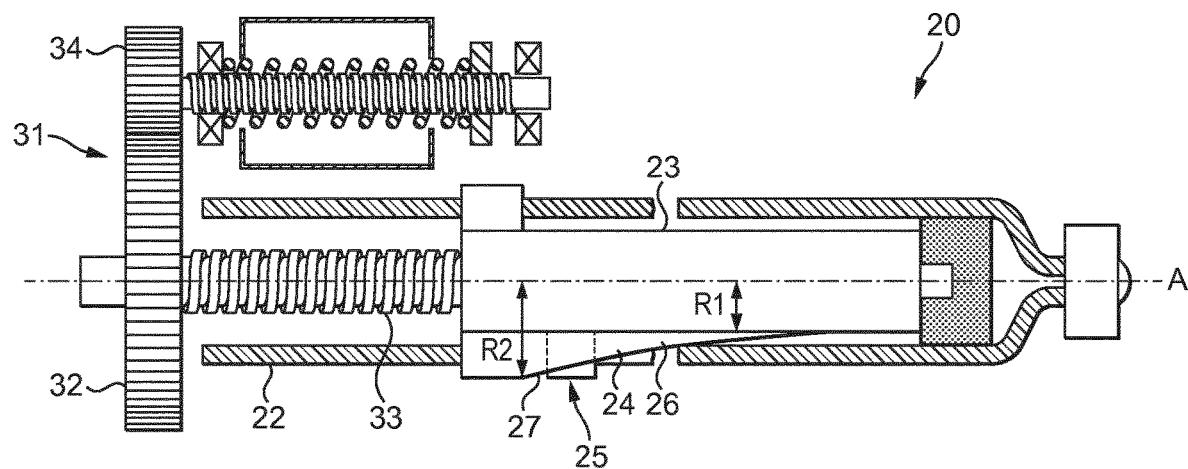
FIG. 2 shows a schematic cross-sectional side view of a medicament delivery device according to a first embodiment.

A medicament delivery device may be configured to inject a medicament into a patient. The medicament delivery device may include a cartridge or syringe in which the medicament is stored prior to being administered. For example, delivery could be sub-cutaneous, intramuscular, or intravenous. Such a device could be operated by a patient or care-giver, such as a nurse or physician, and can include various types of safety syringe, patch pump, pen-injector, or auto-injector. The medicament delivery device may be configured to deliver a liquid drug in a single dose or in multiple doses. The liquid drug may be provided in a container, cartridge or syringe and may be delivered by injection or infusion and may be a mobile or hand-held device. The delivery of the liquid drug by the medicament delivery device may be driven by a motor. The motor may rotate about an axis parallel to the direction in which the liquid drug is moved for delivery to a patient. The motor may be a DC motor. Alternatively, the delivery of the liquid drug by the device may be manually driven by the rotation of, for example, but not limited to, a dial. However, other drive mechanisms for the delivery of the liquid drug to a patient are envisaged such as, for example, but not limited to, pneumatic, hydraulic, electrical, or spring loaded mechanisms.

The delivery devices can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated," whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown in FIGS. 1A & 1B) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown in FIGS. 1A & 1B), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Referring now to FIG. 2, a medicament delivery device 20 includes a housing 22 configured to receive a container of medicament and a piston rod 23 within the housing 22. The piston rod 23 is moveable within the housing 22 and configured to engage a container of medicament when a container of medicament is received within the housing 22. The medicament delivery device 20 further includes a position-sensing mechanism 25 which is configured to detect the position of the piston rod 23 within the housing 22. Thus, the amount of medicament dispensed to a patient can be carefully and accurately monitored.

Figure 4:
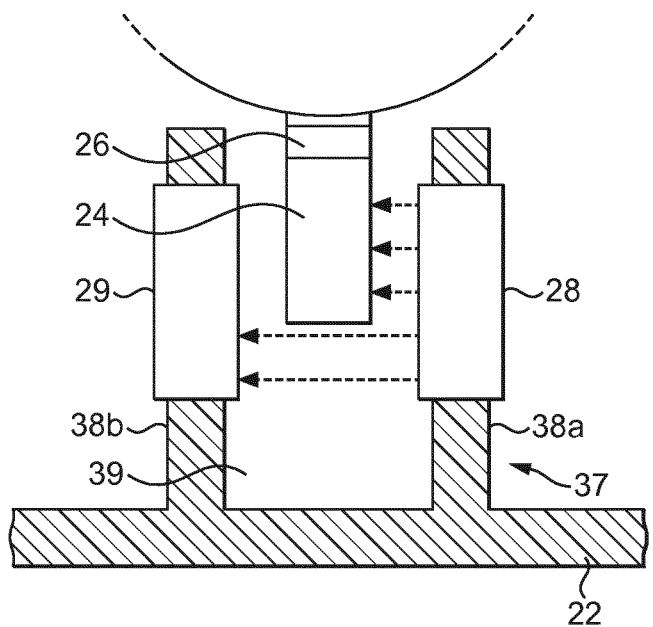
FIG. 4 shows a schematic cross-sectional view along a longitudinal axis of the device.

Referring to FIG. 4, the position-sensing mechanism includes a light source 28 and a sensor 29 disposed proximate the light source. The light source 28 and the sensor 29 are located such that they face one another so that the light emitted by the light source 28 is directed at the sensor 29. The sensor is configured to receive light emitted by the light source 28. The position-sensing mechanism further includes a blocking member 26 that is moveable between the light source 28 and the sensor 29. The blocking member 26 blocks an amount of light emitted by the light source 28 dependent on its position between the light source 28 and the sensor 29 and prevents it from reaching the sensor 29.

Figure 3:
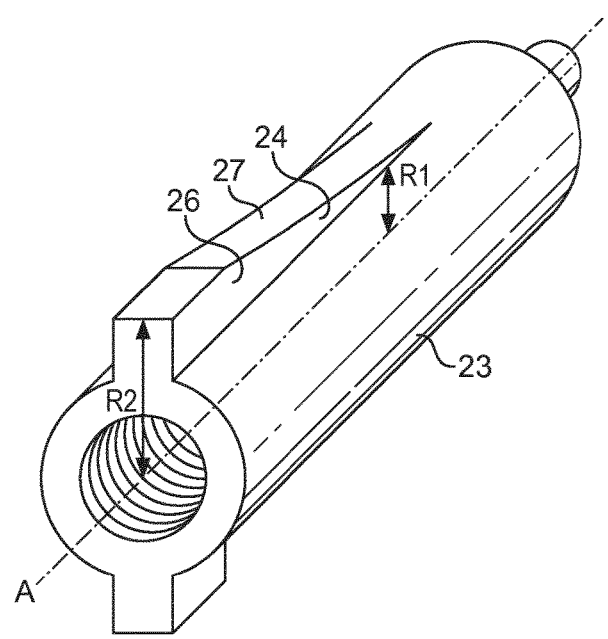
FIG. 3 shows a perspective view of a piston rod removed from the device of FIG. 2.

The medicament delivery device 20 further includes a projecting member 24 that extends from the piston rod 23, as shown in perspective view in FIG. 3. The projection member 24 includes a surface 27 whose distance from an axis A of the piston rod 23 in a longitudinal direction varies along the length of the piston rod 23. That is, the surface 27 is configured such that a distance from the surface to the longitudinal axis of the piston rod 23 varies along the length of the piston rod 23. For example, in the embodiment shown in FIG. 3, the surface 27 of the projecting member 24 is inclined relative to the axis A of the piston rod 23 in the longitudinal direction. That is, the surface 27 is inclined relative to the direction of movement of the piston rod 23 in the housing 22. However, it will be understood that in alternative embodiments, the surface may be shaped differently such that, for example, it includes a series of steps or unevenly spaced castellations. In an alternative embodiment, the surface 27 may not be inclined as explained in further detail hereinafter.

In the present embodiment, the projecting member 24 is the blocking member 26. Thus, the projecting member 24 is configured to be moveable between the light source 28 and the sensor 29. In the present embodiment, the projecting member 24 blocks an amount of light emitted by the light source 28 dependent on its position between the light source 28 and the sensor 29 and prevents it reaching the sensor 29.

The position-sensing mechanism 25 is configured such that a varying light pattern reaches the sensor 29 from the light source 28 dependent on the position of the projecting member 24, acting as the blocking member 26, relative to the light source 28 and the sensor 29. Furthermore, the sensor 29 is configured to detect the varying light pattern received from the light source 28 to determine the position of the piston rod 23 within the housing 22.

In the present embodiment, the light pattern is varied by changing the amount of light that reaches the sensor 29. This is achieved by having an increasing or decreasing area of the projecting member 24, acting as the blocking member 26, between the light source 28 and the sensor 29. In an alternative embodiment, the area of the blocking member 26 that blocks light may stay the same but the change in its position will cause a shadow to fall on a different part of the sensor 29 such that the light pattern detected by the sensor 29 changes. The variation in the amount of shadow detected by the sensor 29 or the variation in the location of the shadow detected by the sensor 29 help the sensor 29 to determine the position of the piston rod 23 within the housing 22.

As previously mentioned, the piston rod 23 is axially moveable within the housing 22. That is, the piston rod 23 can be moved in the longitudinal direction. The piston rod 23 may be configured to push a piston 14 which acts upon a container of medicament when received within the housing 22. However, it will be understood that the piston rod 23 is not limited thereto and may also be, for example, but not limited to, a plunger that pushes a stopper or any component that is axially moveable in the housing, for example, a moveable component which is configured to cause the delivery of medicament to a user or patient.

Referring back to FIG. 2, the piston rod 23 is moveable via a drive mechanism 31. The drive mechanism 31 of the present embodiment includes a gear wheel 32 and a first spindle element 33. The first spindle element 33 is threaded and connected to the piston rod 23 to move the piston rod 23 along the longitudinal axis within the housing 22. The inner surface of the piston rod 23 is threaded to cooperate with the first spindle element 33. The gear wheel 32 may be for example, a dial that is rotated manually by a user of the device 20. Alternatively, the gear wheel 32 may be connected to an electric motor 34 for automatic actuation of the piston rod 23. The electric motor 34 may be a DC motor.

Although, the embodiments illustrate a drive mechanism including a gear wheel and a spindle, other implementations of the drive mechanism are envisaged, for example, but not limited to, pneumatic, hydraulic, electrical, and spring loaded drive mechanisms.

In the embodiment shown in FIGS. 2 to 4, the projecting member 24, acting as the blocking member 26, of the piston rod 23 extends radially from the piston rod 23 and has its inclined surface 27 at its radially outermost position of the projecting member 24. That is, the inclined surface 27 is the surface that is the furthest from the longitudinal axis A of the piston rod 23. Thus, the radial height of the projecting member 24, acting as the blocking member 26, varies along the length of the piston rod 23. In the present embodiment, the projecting member 24 changes the effective radius of the piston rod 23 proportionally along a portion of its length. The piston rod 23 has a radius R1. The projecting member 24 increases the effective radius of the piston rod 23 such that it is at its maximum effective radius R2 at a point furthest from the medicament 36 in the housing 22.

However, in an alternative embodiment, the projecting member 24, acting as the blocking member 26, may be generally rectangular and may include an aperture (not shown) extending through the thickness of the projecting member 24 and extending in the longitudinal direction. The aperture may be, for example, but not limited to, triangular such that the aperture has an internal surface that is inclined with respect to the longitudinal axis of the piston rod 23. Thus, the distance that that aperture extends in the radial direction varies along the length of the piston rod 23. The aperture may either vary in length in the radial direction that it extends or extends at an angle relative to the longitudinal axis A of the piston rod 23.

Figure 5:
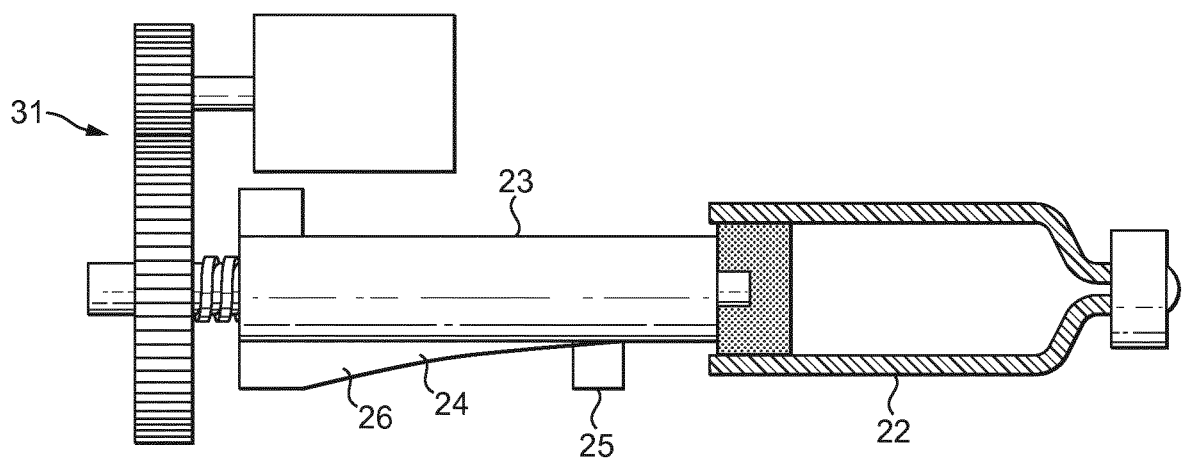
FIG. 5 shows a schematic cross-sectional side view of the first embodiment in a first position before the device has been used.
Figure 6:
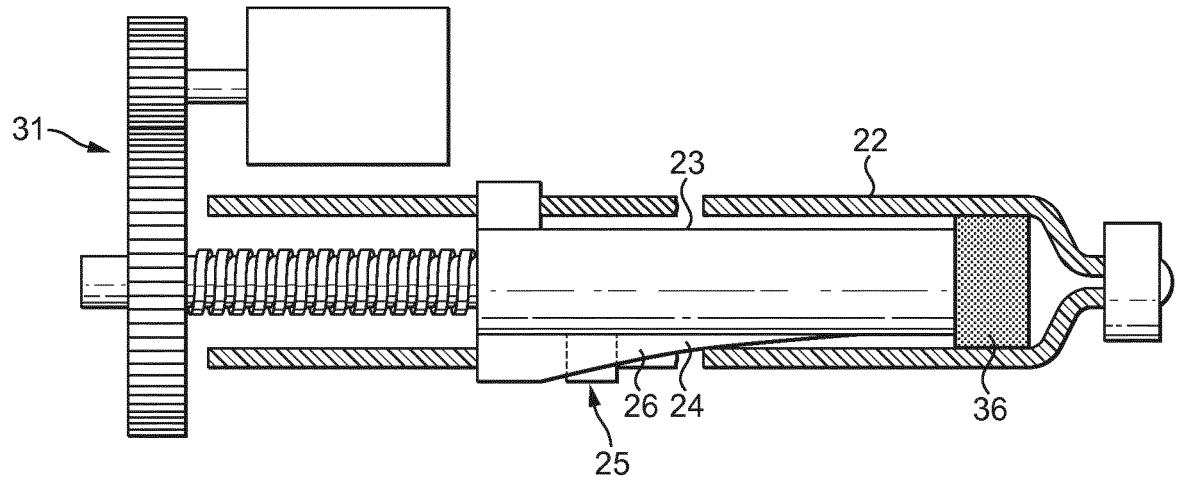
FIG. 6 shows a schematic cross-sectional side view of the first embodiment in a second position after the device has been used.

In the embodiment illustrated in FIGS. 2 and 4, the light source 28 and the sensor 29 are fixed relative to the housing 22. As shown in FIG. 4, the light source 28 and sensor 29 may be arranged such that the light source 28 is located on one side of the projecting member 24, acting as the blocking member 26, and the sensor 29 is located on the opposite side of the projecting member 24. Thus, as the piston rod 23 is moved towards the injection site past the light source 28 and sensor 29, an increasing proportion of the projecting member 24 is present between the light source 28 and the sensor 29, as shown in FIGS. 5 and 6. The further the piston rod 23 is moved towards the injection site, the more light from the light source 28 is blocked and prevented from reaching the sensor 29.

FIG. 5 shows the piston rod 23 in a position before any of the medicament 36 has been dispensed. That is, the drive mechanism 31 has not been activated and the piston rod 23 has not been moved towards the injection site. In this first position, only a small portion of the light source 28 is obscured from the sensor 29 by the projecting member 24, acting as the blocking member 26. FIG. 6 shows the piston rod 23 in a position when the full dose of medicament 36 has been administered. That is, the drive mechanism 31 has been activated and the piston rod 23 has been moved towards the injection site. In the second position, most of the light source 28 is obscured from the sensor 29 by the projection member 24. Therefore, the projecting member 24 blocks different amounts of light from reaching the sensor 29 dependent on the position of the piston rod 23 in the housing 22.

The sensor 29 is configured to detect the varying amount of light that it receives and uses the measurements to determine the position of the piston rod 23 in the housing 22 and therefore, the size of the dose of a medicament that has been administered. The medicament delivery device 20 may include a controller (not shown) which is configured to receive a signal from the sensor 29 and determine the position of the piston rod 23 in dependence on the received signal.

In addition, the controller may be configured to output a position signal to a user interface (not shown) representative of the determined position of the piston rod 23.

In the present embodiment, the sensor 29 and controller are able to determine the position of the piston rod 23 in dependence on the light received by the sensor 29 from the light source 28 and the signal received by the controller because the position-sensing mechanism 25 is "taught." That is, the position-sensing mechanism 25 may be programmed to associate a particular light pattern, or amount of light, with a position of the piston rod 23 within the housing 22. The position of the piston rod 23 within the housing 22 is associated to a dose size. The position-sensing mechanism 25 is programmed by moving the piston rod 23 through the distance for providing a maximum dose or maximum number of doses of a medicament 36. This may be done by a user prior to first use for a reusable device or before final assembly for a disposable device.

In an alternative embodiment, as the piston rod 23 is moved towards the injection site past the light source 28 and sensor 29, a decreasing proportion of the projecting member 24, acting as the blocking member 26, may be present between the light source 28 and the sensor 29. Therefore, the further the piston rod 23 is moved towards the injection site, the less of the light from the light source 28 is blocked and prevented from reaching the sensor 29.

In the embodiments which include an aperture (not shown) in the projecting member 24, acting as the blocking member 26, the radial height of the aperture may be largest at the end of the piston rod 23 furthest from the injection site. Therefore, as the piston rod 23 is moved to administer the medicament, the radial height of the aperture between the light source 28 and the sensor 29 increases so that more light reaches the sensor 29. The sensor 29 will detect the varying amount of light that it receives and uses the measurements to determine the position of the piston rod 23 in the housing 22 and therefore, the size of the dose of the medicament that has been administered. Alternatively, the radial height of the aperture may be largest at the end of the piston rod 23 closest to the injection site.

It will be understood that in one embodiment, the projection member 24, acting as the blocking member 26, may have an inclined surface 27 at its radially outermost position and also include an aperture (not shown) having an inclined surface 27.

As shown in the embodiment in FIG. 4, the housing 22 may include a piston rod guide 37 configured to limit the movement of the piston rod 23 in the housing 22. The piston rod guide 37 includes two projections 38a, 38b between which the projecting member 24 of the piston rod 23 is located. The projections 38a, 38b extend parallel to the longitudinal axis A of the piston rod 23 and define a channel 39 between them. The projections 38a, 38b are configured to restrict rotational movement of the piston rod 23 when the first spindle element 33 is rotated by the gear wheel 32 to force an axial movement of the piston rod 23. One projection 38a may restrict rotational movement of the piston rod 23 in a first direction, for example, the clockwise direction. The other projection 38b may restrict rotational movement of the piston rod 23 in a second direction, for example, the anti-clockwise direction.

In one embodiment, the light source 28 may be mounted in the first projection 38a on one side of the projecting member 24, acting as the blocking member 26. The sensor 29 may be mounted in the second projection 38b on the opposite side of the projecting member 24. The light source 28 and sensor 29 are located opposite each other and face one another so that the light emitted by the light source 28 is directed at the sensor 29. The light source 28 and sensor 29 may be located in the projections 38a, 38b such that they are in a recess and set back from the channel defining surface of the projections 38a, 38b. Thus, the projecting member 24 cannot come into direct contact with the light source 28 or sensor 29 and so misalignment of the sensitive components during use can be avoided. Preferably, a minimum clearance is provided between the light source 28, the sensor 29, and the blocking member 26 (in this embodiment, the projecting member 24) to allow a more accurate measurement of the position of the piston rod 23.

In an alternative embodiment, the light source 28 and the sensor 29 may be on the same side of the blocking element 26. The blocking element 26 may be configured to reflect light and the sensor 29 may determine the position of the piston rod 23 by the varying amount of light that is reflected from the light source 28 to the sensor 29.

Figure 7:
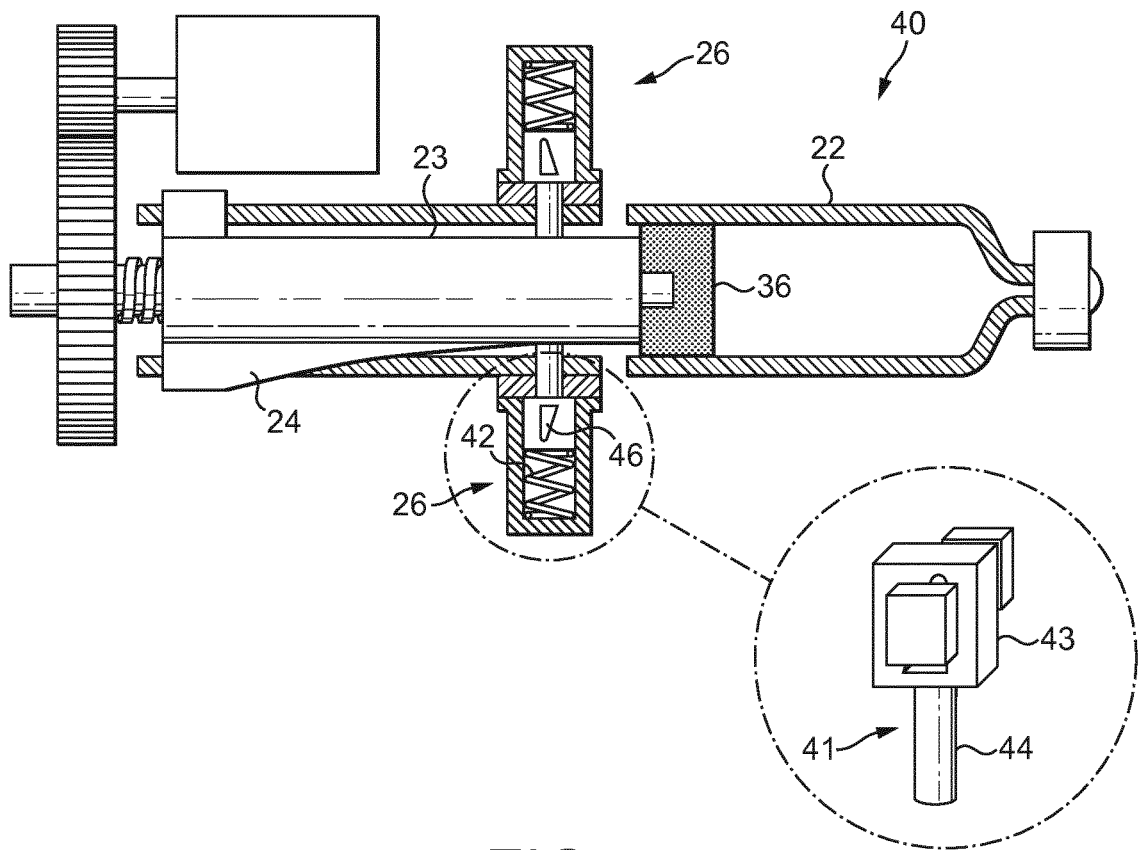
FIG. 7 shows a schematic cross-sectional side view of a second embodiment in a first position before the device has been used.

Referring now to FIG. 7, there is shown a schematic cross-sectional view of a second embodiment of a medicament delivery device 40. The device 40 is generally the same as the embodiment of the device 20 described above and so features and components of the device 40 that are the same as the features and components of the device 20 will retain the same terminology and reference numerals.

In the second embodiment, the medicament delivery device 40 includes a position-sensing mechanism 25 that is configured to provide a precise measurement of the position of the piston rod 23 in the housing 22. In the present embodiment, the blocking element 26 of the position-sensing mechanism 25 includes a first blocking element 41 that is moveable in a direction perpendicular to the direction in which the piston rod 23 is moveable. That is, the first blocking element is moveable towards and away from the piston rod 23. The first blocking element 41 is biased into contact with the surface 27 of the projecting member 24. The first blocking element 41 may be biased towards the piston rod 23 by a biasing member 42 such as, for example, but not limited to a spring. In the present embodiment, the projecting member 24 does not act as a blocking member 26.

The first blocking element 41 includes a first blocking portion 43 and a first piston rod contacting portion 44. The first piston rod contacting portion 44 contacts the surface 27 of the projecting member 24 such that it the first blocking element 41 acts like a cam. In the present embodiment, the light source includes a first light source (28) and the sensor includes a first sensor (29). The first blocking portion 43 is distal to the piston rod 23 and configured such that it is moveable between the first light source 28 and the first sensor 29. The first light source 28 and first sensor 29 may be mounted on the housing 22. The first blocking element 43 is configured such that it blocks light from the first light source 28 from reaching the first sensor 29 so that a varying amount of light reaches the first sensor 29 from the first light source 28 dependent on the position of the first blocking element 43, which is itself dependent on the position of the piston rod 23 in the housing 22. Therefore, which part of the surface 27 of the projecting member 24 the first piston rod contacting portion 44 of the first blocking element 41 is in contact with determines the position of the first blocking element 43 between the first light source 28 and the first sensor 29. Preferably, the first blocking element 41 extends radially relative to the piston rod 23.

In the second embodiment, the first light source 28 and first sensor 29 are also fixed relative to the housing 22. The first light source 28 and the first sensor 29 are arranged such that the first light source 28 is on a first side of the first blocking element 41 and the first sensor 29 is located on the opposite side of the first blocking element 41. Preferably, the first light source 28 and the first sensor 29 are arranged parallel to the direction of movement of the first blocking element 41 such that the travel path of light from the first light source 28 to the first sensor 29 is perpendicular to the direction of movement of the first blocking element 41.

Figure 8:
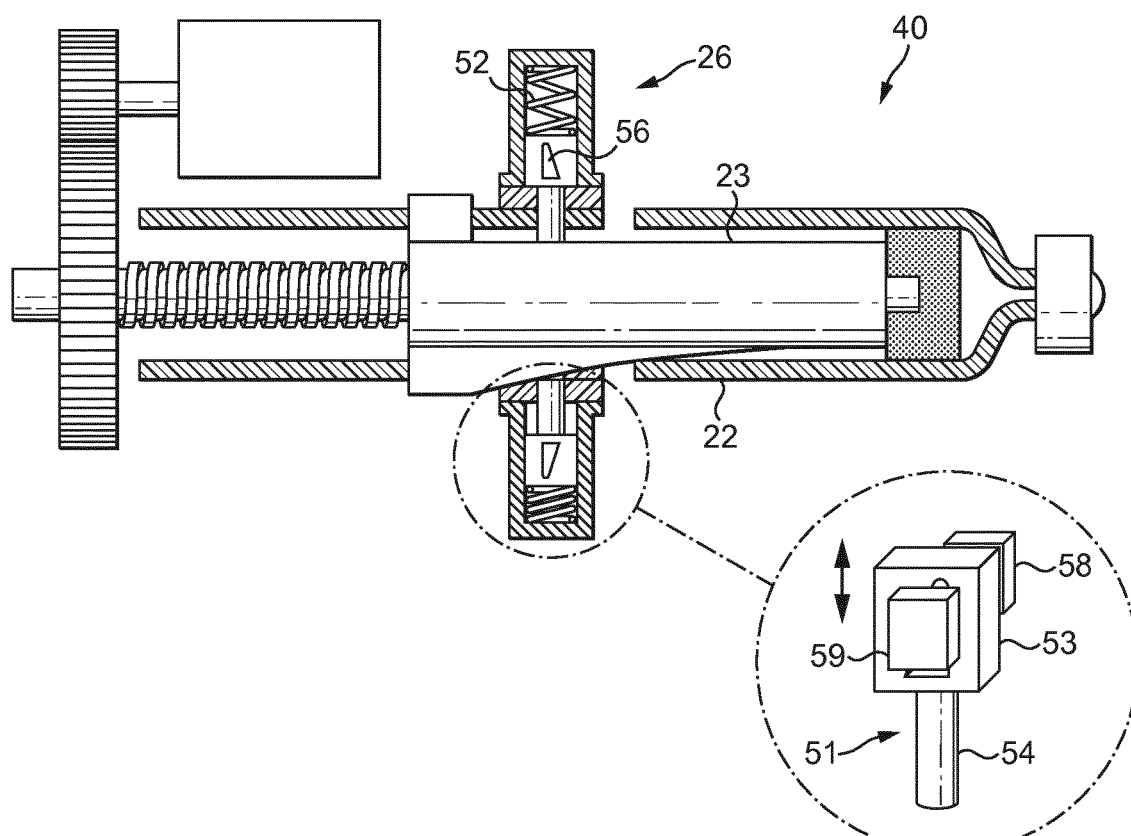
FIG. 8 shows a schematic cross-sectional side view of the second embodiment in a second position after the device has been used.

As illustrated in FIGS. 7 and 8, the first blocking element 41 includes an aperture 46. The aperture 46 has a cross-sectional area that varies in the direction of movement of the first blocking element 41 to block different amounts of light dependent on the position of the first blocking element 41 in the direction of movement. The aperture 46 extends through the thickness of the first blocking portion 43 of the first blocking element 41 in the direction of the travel path of the light from the first light source 28 to the first sensor 29. The aperture 46, may be for example, but not limited to, triangular.

In the present embodiment, the triangular aperture 46 is configured such that it has a surface configured such that a distance from the surface to the longitudinal axis A of the piston rod 23 varies. That is, the aperture 46 is arranged such that the base of the triangular aperture 46 is proximate the piston rod 23 and the tip of the triangular aperture 46 is distal to the piston rod 23.

Thus, when the first piston rod contacting portion 44 abuts the piston rod 23 at the point where it has its smallest effective radius R1, the first blocking portion 43 protrudes into the space between the first light source 28 and the first sensor 29 by a minimal amount. This means that light can pass from the first light source 28 to the first sensor 29 through the tip of the triangular aperture 46 and so a minimal amount of light reaches the first sensor 29. Thus, the first sensor 29 determines that the piston rod 23 is in a first position where the medicament 36 has not been administered, as shown in FIG. 7. When the first piston rod contacting portion 44 abuts the piston rod 23 at the point where it has its largest effective radius, the first blocking portion 43 protrudes into the space between the first light source 28 and the first sensor 29 by a maximum amount. This means that light can pass from the first light source 28 to the first sensor 29 through the base or the entire triangular aperture 46 and so a maximum amount of light reaches the first sensor 29. Thus, the first sensor 29 determines that the piston rod 23 is in a second position where the medicament 36 has been administered, as shown in FIG. 8.

In an alternative embodiment, the first blocking portion 43 may not include an aperture 46. Instead, the first blocking portion 43 may be configured such that an external surface, such as the surface furthest from the piston rod 23, is configured such that a distance from the surface to the longitudinal axis of the piston rod 23 varies along the surface of the first blocking portion 43. For example, the external surface of the first blocking portion 43 that is furthest from the piston rod 23 may be inclined with respect to the direction of movement of the first blocking element 41 and/or the piston rod 23.

In addition, the blocking member 26 of the position-sensing mechanism 25 further includes a second blocking element 51 located on the opposite side of the piston rod 23 to the first blocking element 41. The second blocking element 51 is moveable in a direction perpendicular to the direction of movement in which the piston rod 23 is moveable. That is, the second blocking element 51 is moveable towards and away from the piston rod 23. The second blocking element 51 is biased into contact with the body of the piston rod 23. The second blocking element 51 may be biased towards the piston rod 23 by a biasing member 52 such as, for example, but not limited to a spring.

In the present embodiment, the light source further includes a second light source (58) and the sensor further includes a second sensor (59). The second blocking element 51 includes a second blocking portion 53 and a second piston rod contacting portion 54. The second piston rod contacting portion 54 contacts the body of the piston rod 23 such that the second blocking element 51 acts like a cam. The second blocking portion 53 is distal to the piston rod 23 and configured such that it is moveable between the second light source 58 and the second sensor 59 mounted on the housing 22. The second blocking portion 53 is configured such that it blocks light from the second light source 58 from reaching the second sensor 59 so that a varying amount of light reaches the second sensor 59 from the second light source 58 dependent on the position of the second blocking portion 51, which is itself dependent on the position of the piston rod 23 in the housing 22. Therefore, which part of the body of the piston rod 23 the second piston rod contacting portion 54 of the second blocking element 51 is in contact with determines the position of the second blocking element 53 between the second light source 58 and second sensor 59. Preferably, the second blocking element 51 extends radially relative to the piston rod 23.

In the second embodiment, the second light source 58 and second sensor 59 are also fixed relative to the housing 22. The second light source 58 and second sensor 59 are arranged such that the second light source 58 is on a first side of the second blocking element 51 and the second sensor 59 is located on the opposite side of the second blocking element 51. Preferably, the second light source 58 and the second sensor 59 are arranged parallel to the direction of movement of the second blocking element 51 such that the travel path of light from the second light source 58 to the second sensor 59 is perpendicular to the direction of movement of the second blocking element 51.

As illustrated in FIGS. 7 and 8, the second blocking element 51 includes an aperture 56. The aperture 56 has a cross-sectional area that varies in the direction of movement of the second blocking element 51 to block different amounts of light dependent on the position of the second blocking element 51 in the direction of movement. The aperture 56 extends through the thickness of the second blocking portion 53 of the second blocking element 51 in the direction of the travel path of the light from the second light source 58 to the second sensor 59. The aperture 56, may be for example, but not limited to, triangular.

In the present embodiment, the triangular aperture 56 is configured such that it has a surface configured such that a distance from the surface to the longitudinal axis A of the piston rod 23 varies. That is, the aperture 56 is arranged such that the base of the triangular aperture 56 is proximate the piston rod 23 and the tip of the triangular aperture 56 is distal to the piston rod 23.

In an alternative embodiment, the apertures 46, 56 may be, for example, but not limited to, rectangular, and the position of the rectangular pattern of light on the sensors 29, 59 may be used to determine the position of the piston rod 23 in the housing 22.

In an alternative embodiment, the second blocking portion 53 may not include an aperture 56. Instead, the second blocking portion 53 may be configured such that an external surface, such as the surface furthest from the piston rod 23, is configured such that a distance from the surface to the longitudinal axis of the piston rod 23 varies along the surface of the second blocking portion 53. For example, the external surface of the second blocking portion 53 that is furthest from the piston rod 23 may be inclined with respect to the direction of movement of the second blocking element 51 and/or the piston rod 23.

The second blocking element 51 is configured to give a differential reading to compensate for radial movement of the piston rod 23 within the housing 22 and manufacturing defects. Thus, the position of the piston rod 23 as determined by the first sensor 29 can be corrected and made more precise by subtracting the measurement made by the second sensor 59. Therefore, a more precise measurement of exactly how much of the medicament 36 in the device 40 has been administered is achievable.

The sensor 29, 59 may be a position sensitive detector including a laminar semi-conductor that changes its local resistance in response to light. The change in resistance changes the electron flow between electrodes. The location of the light in both the X and Y directions can be computed using a current divider formula so determine the position of the piston rod 23 in the housing 22. Position sensitive detectors are advantageous as the measurement process is continuous. Alternatively, the sensor 29, 59 may be a charge-coupled device including a matrix of photosensitive cells known as pixels. Each pixel is connected to a capacitor which is charges during exposure to light. A converter determines the charge of each pixel and converts the charge into a value. The charge of the pixels can be used to determine the position of the piston rod 23 in the housing 22. It will be understood that alternative sensors may be used.

In an alternative embodiment, it will be understood that the second blocking element 51, second light source 58, and second sensor 59 are not essential.

Figure 9:
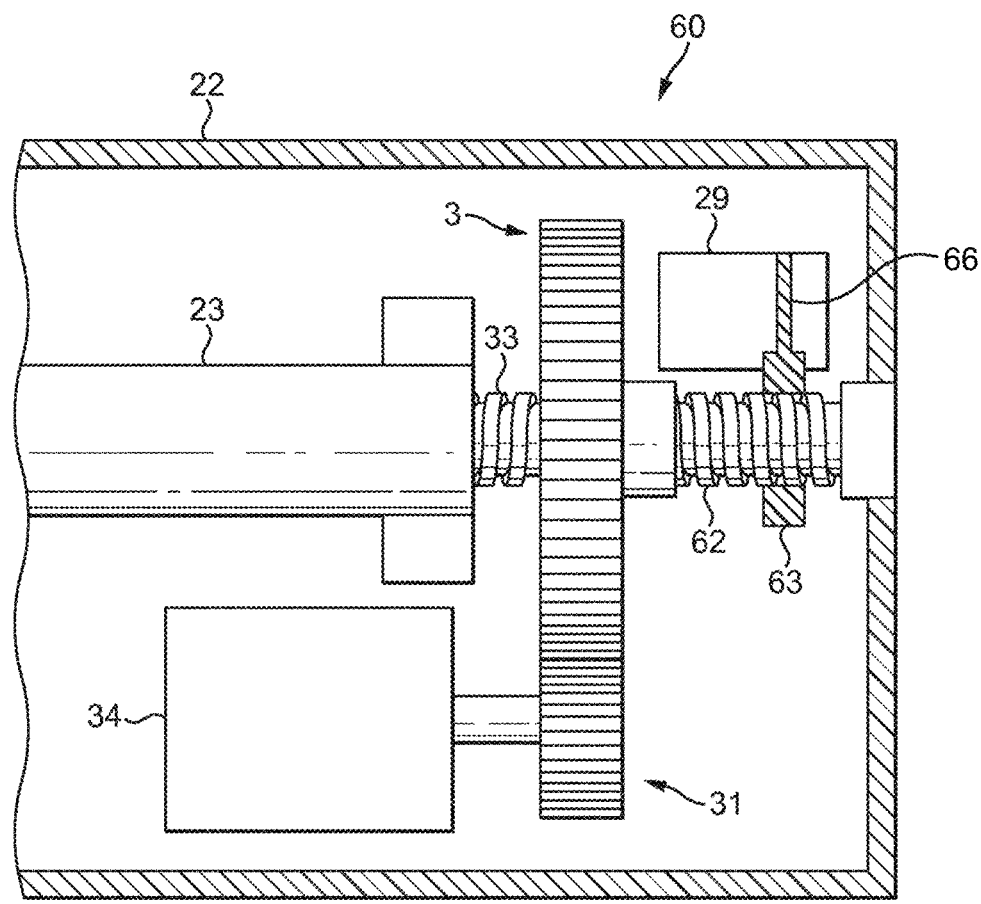
FIG. 9 shows an enlarged schematic cross-sectional side view of a third embodiment.

Referring now to FIG. 9, there is shown a schematic cross-sectional view of a third embodiment of a medicament delivery device 60. The device 60 is generally the same as the embodiment of the device 20 described above and so features and components of the device 60 that are the same as the features and components of the device 20 will retain the same terminology and reference numerals.

In the third embodiment, the medicament delivery device 60 further includes a component 63 that is moveable within the housing 22 and includes a blocking member 66 configured to block light passing from the light source, not shown in FIG. 9, to the sensor 29.

The component 63 is moveable in the longitudinal direction. That is, the component 63 is moveable in the same direction as the piston rod 23. In an alternative embodiment, the component 63 may be moveable in a direction at an angle to the longitudinal direction, for example, but not limited to, perpendicular.

In the third embodiment, the component 63 acts as a dose nut. That is, the component 63 is used to determine the position of the piston rod 23 in the housing 22 and, therefore, the size of the dose that has been administered to a patient or a user. The component 63 is located on the opposite side of the drive mechanism 31 to the piston rod 23. The component 63 includes the blocking member 66 which, in the present embodiment, extends in the radial direction. In the present embodiment, shown in FIG. 9, the blocking member 66 is a rectangular shaped protrusion. However, it will be understood that in alternative embodiments, the shape of the blocking member 66 may differ.

The light source and the sensor 29 are positioned such that when the component 63 is moved in the longitudinal direction, the blocking member 66 blocks light emitted from the light source from reaching different parts of the sensor 29. As the blocking member 66 is a rectangular shaped protrusion, the amount of light that reaches the sensor 29, or the area of the sensor that light reaches, typically does not vary but the light pattern typically does. Therefore, the sensor 29 and controller (not shown) are configured to determine the position of the component 63 in the housing 22 based upon the differing pattern of light that reaches the sensor 29 from the light source. The position of the component 63 correlates to the position of the piston rod 23 in the housing 22.

As within the first embodiment, the housing 22 may include a piston rod guide, similar to the piston rod guide 37 shown in FIG. 4, configured to limit the rotational movement of the component 63 in the housing 22. The piston rod guide may include at least two projections 38a, 38b, shown in FIG. 4, between which the blocking member 66 of the component 63 is at least partially located. The projections 38a, 38b, may extend parallel to the direction in which the component 63 is moveable, that is, the longitudinal direction/axis of the piston rod 23, and define a channel between them in which the blocking member 66 is at least partially received.

Furthermore, in the third embodiment of the disclosure, the drive mechanism 31 of the medicament delivery device 60 includes a second spindle element 62. The second spindle element 62 extends from the gear wheel 32 in a direction opposite to the first spindle element 33 such that the two spindle elements 33, 62 are on opposing sides of the gear wheel 32. That is, the second spindle element 62 is located on the opposite side of the gear wheel 32 to the piston rod 23. Both spindle elements 33, 62 extend from the centre of the gear wheel 32.

The second spindle element 62 is threaded and connected to the component 63 whose inner surface is threaded to cooperate with the second spindle element 62. The projections 38a, 38b are configured to restrict rotational movement of the component 63 when the second spindle element 62 is rotated by the gear wheel 32 to force an axial movement of the component 63. One projection 38a may restrict rotational movement of the component 63 in a first direction, for example, the clockwise direction. The other projection 38b may restrict rotational movement of the component 63 in a second direction, for example, the anti-clockwise direction. In some embodiments, such as one used disposable devices, only one projection may be needed.

The gear wheel 32 may be for example, a dial that is rotated manually by a user of the device. Alternatively, the gear wheel 32 may be connected to an electric motor 34 for automatic actuation of the piston rod 23. It will be understood that in alternative embodiments, other drive mechanisms may be used, as explained above.

In the present embodiment, the size of the sensor 29 may be matched to the thread height of the second spindle element 62. The thread height and pitch of the second spindle element 62 may in turn be designed to a specific ratio of the thread height and pitch of the first spindle element 33 such that, for example, but not limited to, one turn of the gear wheel 32 moves the piston rod 23 two units of measurement whilst the component 63 is only moved one unit of measurement. Thus, the dimensions of the medicament delivery device 60 can be kept as small as possible whilst retaining an accurate measurement of the dose administered.

Figure 10:
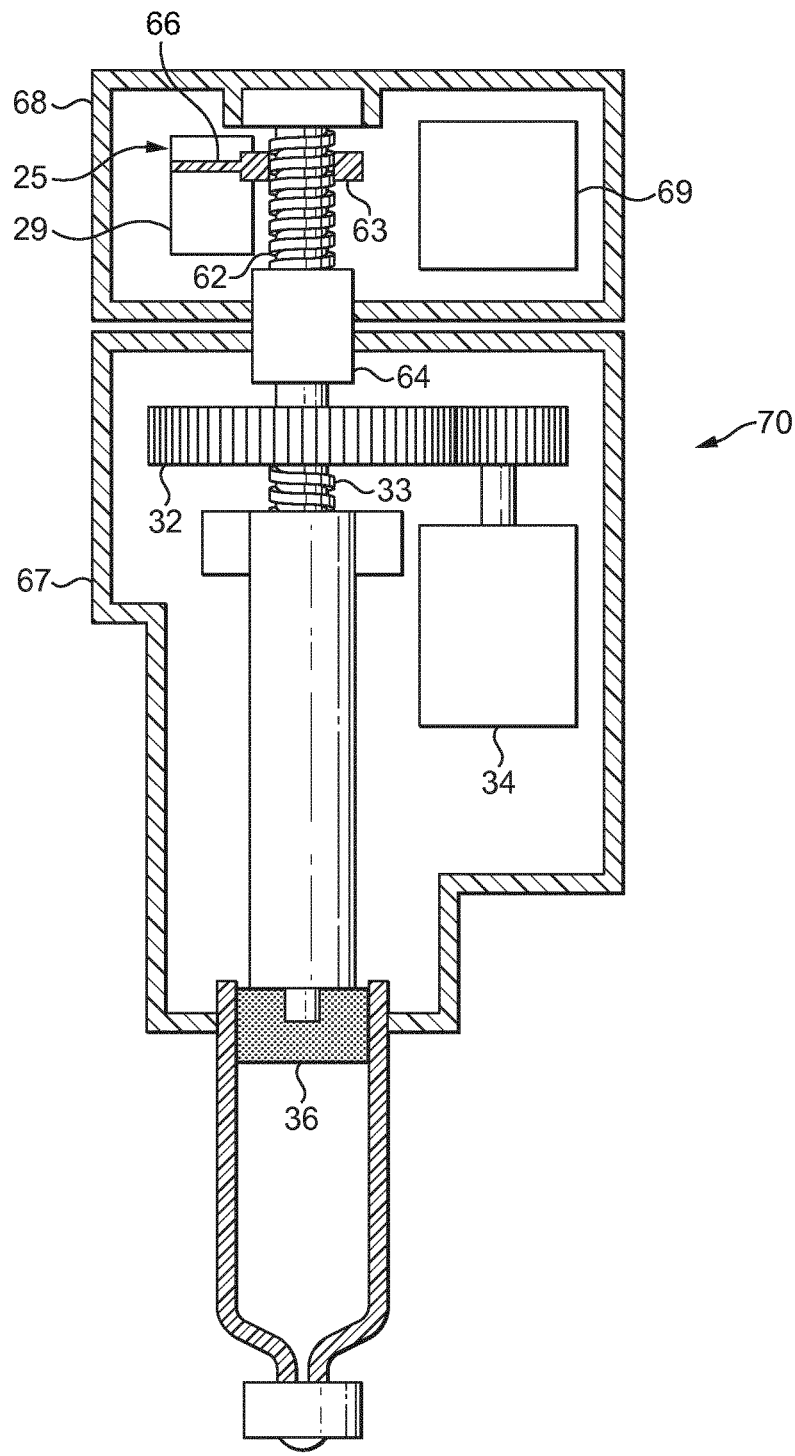
FIG. 10 shows a schematic cross-sectional side view of a fourth embodiment.

Referring now to FIG. 10, there is shown a schematic cross-sectional view of a fourth embodiment of a medicament delivery device 70. The device 70 is generally the same as the embodiment of the device 60 described above and so features and components of the device 70 that are the same as the features and components of the device 60 will retain the same terminology and reference numerals.

In the fourth embodiment, the second spindle element 62 includes a separable connection 64. The separable connection 64 may be in the form of, for example, but not limited to, a clutch. The separable connection 62 may be detached and reattached multiple times. In addition, the housing 22 is formed by two portions 67, 68. A first portion 67 includes the gear wheel 32, first spindle element 33, piston rod 23, space for receiving a container of medicament 36, and a motor. The second portion 68 of the housing 22 includes the component 63, the position-sensing mechanism 25, including the blocking member 26, the light source, and the sensor 29, and the second spindle element 62. The first and second portions 67, 68 may be detached and reattached multiple times. The second portion 68 may also includes an electronic display 69 for displaying information such as piston rod 23 or component 63 position and/or the dose size already administered or left within a medicament delivery device 70.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastrointestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not include a full-length antibody polypeptide, but that still includes at least a portion of a full-length antibody polypeptide that is capable of binding to an antigen. Antibody fragments can include a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations including (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. A medicament delivery device comprising:
   a housing configured to receive a container of medicament;
   a piston rod moveable within the housing and configured to engage the container of medicament when the container of medicament is disposed within the housing; and
   a position-sensing mechanism configured to detect a position of the piston rod within the housing, the position-sensing mechanism comprising:
      a light source configured to emit light;
      a sensor disposed proximate the light source and configured to receive light emitted by the light source; and
      a blocking member extending outward relative the piston rod, the blocking member being (i) moveable between the light source and the sensor, (ii) movably coupled to the piston rod, and (iii) configured to block a portion of the light emitted by the light source, thereby preventing the portion of the light from reaching the sensor;
   wherein the position-sensing mechanism is configured such that a varying light pattern which reaches the sensor is dependent on the position of the blocking member relative to the light source and the sensor; and
   wherein the sensor is configured to detect the varying light pattern received to determine the position of the piston rod within the housing, wherein a particular varying light pattern is associated with a particular position of the piston rod within the housing.

2. The medicament delivery device according to claim 1, further comprising a controller configured to receive a signal from the sensor and determine the position of the piston rod based on the received signal.

3. The medicament delivery device according to claim 2, wherein the controller is configured to output a position signal to a user interface representative of the determined position of the piston rod.

4. The medicament delivery device according to claim 1, wherein the piston rod is threadingly engaged with a drive mechanism and is configured to act upon a piston of the container of medicament within the medicament delivery device when the container of medicament is disposed within the housing and the drive mechanism is activated.

5. The medicament delivery device according to claim 4, wherein the blocking member extends from a component on an opposite side of the drive mechanism to the piston rod, and the component is engaged with the drive mechanism such that it is moveable within the housing when the drive mechanism is activated.

6. The medicament delivery device according to claim 5, wherein the position-sensing mechanism and the component are located in a separable portion of the housing and the drive mechanism comprises a separable connection which is configured to separably connect a first part of the drive mechanism which engages the piston rod in a first portion of the housing and a second part of the drive mechanism that engages the component in a second portion of the housing.

7. The medicament delivery device according to claim 1, further comprising a projecting member extending from the piston rod, the projecting member having a surface configured such that a distance from the surface to a longitudinal axis of the piston rod varies along a length of the piston rod.

8. The medicament delivery device according to claim 7, wherein the projecting member is part of the blocking member and is configured to be moveable between the light source and the sensor.

9. The medicament delivery device according to claim 7, wherein the surface of the projecting member is inclined relative to a direction of movement of the piston rod in the housing.

10. The medicament delivery device according to claim 7, wherein the blocking member of the position-sensing mechanism comprises a first blocking element that is moveable in a direction perpendicular to the direction in which the piston rod is moveable, the first blocking element being biased into contact with the surface of the projecting member.

11. The medicament delivery device according to claim 10, wherein the light source comprises a first light source, the sensor comprises a first sensor, and
   wherein the first blocking element comprises a first blocking portion configured such that the first blocking portion is moveable between the first light source and the first sensor.

12. The medicament delivery device according to claim 11, wherein the first light source and the first sensor are arranged such that the first light source is on a first side of the first blocking element and the first sensor is on the opposite side of the first blocking element.

13. The medicament delivery device according to claim 11, wherein the first blocking element comprises an aperture having a cross-sectional area that varies in a direction of movement of the first blocking element configured to block different amounts of light based on a position of the first blocking element in the direction of movement of the first blocking element.

14. The medicament delivery device according to claim 11, wherein a surface of the first blocking portion is configured such that a distance from the surface to a longitudinal axis of the piston rod varies along the surface.

15. The medicament delivery device according to claim 11, wherein the position-sensing mechanism further comprises a second blocking element located on an opposite side of the piston rod to the first blocking element, the second blocking element being moveable in a direction perpendicular to the direction in which the piston rod is moveable and the second blocking element being biased into contact with a body of the piston rod.

16. The medicament delivery device according to claim 15, wherein the light source comprises a second light source, the sensor comprises a second sensor, the second blocking element comprises a second blocking portion, and
wherein the second blocking element is moveable between the second light source and the second sensor and the second blocking element is configured such that a varying light pattern reaches the second sensor from the second light source dependent on the position of the second blocking portion which is dependent on the position of the piston rod in the housing.

17. The medicament delivery device according to claim 16, wherein the second light source and the second sensor are arranged such that the second light source is on a first side of the second blocking element and the second sensor is on the opposite side of the second blocking element.

18. The medicament delivery device according to claim 16, wherein the second blocking element comprises an aperture having a cross-sectional area that varies in a direction of movement of the second blocking element configured to block different amounts of light based on the position of the second blocking element in the direction of movement of the second blocking element.

19. The medicament delivery device according to claim 16, wherein a surface of the second blocking portion is configured such that a distance from the surface to a longitudinal axis of the piston rod varies along the surface.

20. The medicament delivery device according to claim 16, wherein a surface of the first blocking portion is inclined relative to a direction of movement of the first blocking element and a surface of the second blocking portion is inclined relative to a direction of movement of the second blocking element.

21. The medicament delivery device according to claim 1, wherein the varying light pattern represents a first portion of the sensor where the light reaches the sensor and a second portion of the sensor where the portion of the light does not reach the sensor.

22. The medicament delivery device according to claim 21, wherein the blocking member prevents the portion of the light from reaching the sensor and causes a shadow to fall on the second portion of the sensor.

23. The medicament delivery device according to claim 1, wherein the varying light pattern represents a first location of pixels of the sensor where the light reaches the sensor and a second location of pixels on the sensor where the portion of the light does not reach the sensor.

24. A medicament delivery device comprising:
a housing configured to receive a container of medicament;
a piston rod moveable within the housing and configured to engage the container of medicament when the container of medicament is disposed within the housing; and
a position-sensing mechanism configured to detect a position of the piston rod within the housing, the position-sensing mechanism comprising:
a light source configured to emit light;
a sensor disposed proximate the light source and configured to receive light emitted by the light source; and
a blocking member (i) moveable between the light source and the sensor, (ii) movably coupled to the piston rod, and (iii) configured to block a portion of the light emitted by the light source, thereby preventing the portion of the light from reaching the sensor;
wherein the position-sensing mechanism is configured such that a varying light pattern which reaches the sensor is dependent on the position of the blocking member relative to the light source and the sensor;
wherein the sensor is configured to detect the varying light pattern received to determine the position of the piston rod within the housing, wherein a particular varying light pattern is associated with a particular position of the piston rod within the housing;
wherein the piston rod is threadingly engaged with a drive mechanism and is configured to act upon a piston of the container of medicament within the medicament delivery device when the container of medicament is disposed within the housing and the drive mechanism is activated; and
wherein the blocking member extends from a component on an opposite side of the drive mechanism to the piston rod, and the component is engaged with the drive mechanism such that it is moveable within the housing when the drive mechanism is activated.

25. A medicament delivery device comprising:
a housing configured to receive a container of medicament;
a piston rod moveable within the housing and configured to engage the container of medicament when the container of medicament is disposed within the housing;
a position-sensing mechanism configured to detect a position of the piston rod within the housing, the position-sensing mechanism comprising:
a light source configured to emit light;
a sensor disposed proximate the light source and configured to receive light emitted by the light source; and
a blocking member (i) moveable between the light source and the sensor, (ii) movably coupled to the piston rod, and (iii) configured to block a portion of the light emitted by the light source, thereby preventing the portion of the light from reaching the sensor; and
a projecting member extending from the piston rod, the projecting member having a surface configured such that a distance from the surface to a longitudinal axis of the piston rod varies along a length of the piston rod, the surface of the projecting member being inclined relative to a direction of movement of the piston rod in the housing;

wherein the position-sensing mechanism is configured such that a varying light pattern which reaches the sensor is dependent on the position of the blocking member relative to the light source and the sensor; and wherein the sensor is configured to detect the varying light pattern received to determine the position of the piston rod within the housing, wherein a particular varying light pattern is associated with a particular position of the piston rod within the housing.

* * * * *